US009360451B2

(12) United States Patent
Chen et al.

(10) Patent No.: US 9,360,451 B2
(45) Date of Patent: Jun. 7, 2016

(54) METHOD FOR DIAGNOSING WHETHER A SUBJECT IS AT HIGH RISK FOR DEVELOPING ATHEROSCLEROTIC VASCULAR DISEASE

(71) Applicant: China Medical University, Taichung (TW)

(72) Inventors: Chao-Jung Chen, Taichung (TW); Chao-Yuh Yang, Taichung (TW); Chiz-Tzung Chang, Taichung (TW)

(73) Assignee: CHINA MEDICAL UNIVERSITY, Taichung (TW)

( * ) Notice: Subject to any disclaimer, the term of this patent is extended or adjusted under 35 U.S.C. 154(b) by 619 days.

(21) Appl. No.: 13/773,820

(22) Filed: Feb. 22, 2013

(65) Prior Publication Data

US 2014/0183041 A1   Jul. 3, 2014

(30) Foreign Application Priority Data

Dec. 28, 2012   (TW) .............................. 101150905 A

(51) Int. Cl.
*G01N 27/447* (2006.01)
(52) U.S. Cl.
CPC ................................ *G01N 27/44747* (2013.01)
(58) Field of Classification Search
CPC . G01N 27/447; G01N 33/92; B01D 15/3385; B01D 57/02
See application file for complete search history.

(56) References Cited

FOREIGN PATENT DOCUMENTS

WO    WO 2012/145037    * 10/2012

OTHER PUBLICATIONS

L. Allard, et al. "ApoC-I and ApoC-III as potential plasmatic biomarkers to distinguish between ischemic and hemorrhagic stroke", Proteomics, vol. 4, 2004, p. 2242-2251.*
Invitrogen, "NuPage® Technical Guide: General information and protocols for using the Nupage® electrophoresis system", Manual part No. IM-1001, Oct. 29, 2010.*
Hoang et al., "Advanced glycation of apolipoprotein A-I impairs its anti-atherogenic properties" Diabetologia 50.8 (2007): 1770-1779.
Pankhurst et al., "Characterizatio of specifically oxidized apolipoproteins in mildly oxidized high density lipoprotein" Journal of lipid research 44.2 (2003): 249-355.

* cited by examiner

*Primary Examiner* — J. Christopher Ball
(74) *Attorney, Agent, or Firm* — McClure, Qualey & Rodack, LLP

(57) ABSTRACT

A method for diagnosing whether a subject is at high risk for developing atherosclerotic vascular disease (ASVD) is provided. The method comprises the following steps: (1) providing a specimen from a subject; (2) analyzing the specimen by using a gradient gel electrophoresis analysis; and (3) based on the result of the gel electrophoresis analysis in step (2), determining if the subject is at high risk for developing atherosclerotic vascular disease.

8 Claims, 3 Drawing Sheets

METHOD FOR DIAGNOSING WHETHER A SUBJECT IS AT HIGH RISK FOR DEVELOPING ATHEROSCLEROTIC VASCULAR DISEASE

CROSS-REFERENCES TO RELATED APPLICATIONS

This application claims the benefit of Taiwan Patent Application No. 101150905, filed on Dec. 28, 2012, in the Taiwan Intellectual Property Office, the disclosure of which is incorporated herein in its entirety by reference.

BACKGROUND OF THE INVENTION

1. Field of the Invention

The present invention relates to a method for diagnosing whether a subject is at a high risk for developing atherosclerotic vascular disease (ASVD), especially for diagnosing whether a subject has a predisposition for developing atherosclerotic vascular disease by using a gradient gel electrophoresis analysis.

2. Descriptions of the Related Art

Atherosclerosis is a chronic inflammatory process primarily caused by the deposit of cholesterol, lipid, connective tissue and calcium carbonate in the arteries, which leads to the hardening and thickening of the arterial walls and the loss of arterial elasticity. The risk factors for atherosclerosis include diseases (e.g., diabetes, uremia, and primary hyperlipidemia), smoking, heredity, obesity, high-calorie and high-fat diets, etc.

Arterial hardening (atherosclerosis) may progress without symptoms for decades, and symptoms normally express as the level of arterial hardening become severe. Various diseases may be caused by arterial hardening, such as angina pectoris, coronary artery disease (CAD), myocardial infraction, transient ischemic attack, ischemic stroke, carotid artery disease, and peripheral arterial occlusive disease.

The diagnostic methods for atherosclerotic vascular disease presently used in clinical settings include coronary angiography, carotid ultrasound detection, intravascular ultrasound detection, computed tomography, magnetic resonance imaging, etc. However, these traditional diagnostic methods are time-consuming, expensive, and may result in a delayed diagnosis. Therefore, there is still a need for an easy and rapid method for diagnosing whether a subject is at high risk for developing atherosclerotic vascular disease so as to adopt proper preventive and/or treatment approaches in advance.

The present invention is completed and directed to the above demands. The inventors of the present invention found that when a specimen from a subject suffering from atherosclerotic vascular disease is analyzed by a gradient gel electrophoresis analysis, the electrophoresis gel will show a specific protein band pattern. It was further confirmed that if a specimen from a subject who does not suffer from atherosclerotic vascular disease is analyzed by a gradient gel electrophoresis analysis and the result shows the specific protein band pattern, the subject is at high risk for developing atherosclerotic vascular disease. Therefore, the gradient gel electrophoresis analysis can be used to rapidly and preliminary determine if a subject is at high risk for developing atherosclerotic vascular disease.

SUMMARY OF THE INVENTION

The primary objective of this invention is to provide a method for diagnosing whether a subject is at a high risk for developing atherosclerotic vascular disease, comprising the following steps: (1) providing a specimen from a subject; (2) analyzing the specimen by using a gradient gel electrophoresis analysis; and (3) based on the results of the gel electrophoresis analysis in step (2), determining if the subject is at high risk for developing atherosclerotic vascular disease.

The detailed technical features and preferred embodiments of the subject invention are described in the following paragraphs accompanying the appended drawings for people skilled in this field to well appreciate the features of the claimed invention.

DESCRIPTION OF THE PREFERRED EMBODIMENT

Figure 1A:
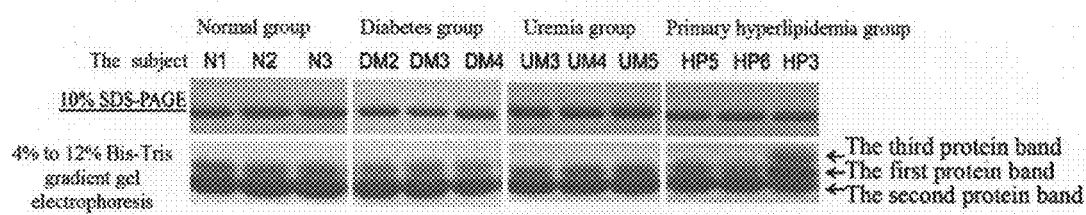
FIGS. 1A and 1B are gel electrophoresis pictures of high-density lipoprotein.

The following will describe some embodiments of the present invention in detail. However, without departing from the spirit of the present invention, the present invention may be embodied in various modifications and should not be limited to the embodiments described in the specification. In addition, unless otherwise stated herein, the terms "a (an)", "the", or the like used in this specification (especially in the claims hereinafter) shall be understood to encompass both the singular and plural forms.

Atherosclerotic vascular disease refers to a disease caused by atherosclerosis, including angina pectoris, coronary artery disease, myocardial infraction, transient ischemic attack, ischemic stroke, carotid artery disease, and peripheral arterial occlusive disease. Mild atherosclerosis may remain asymptomatic until the blood flow volume of an organism is restricted or completely occluded. Therefore, a method for rapidly and accurately detecting those at high risk for developing atherosclerotic vascular disease is still needed.

Gradient gel electrophoresis refers to gel electrophoresis performed by using a gel with a concentration that increases gradually from top to bottom. Because the pore size in the gel of a gradient gel electrophoresis decreases from top to bottom, gradient gel electrophoresis can significantly increase the resolution of protein separation as compared to traditional gel electrophoresis. The inventors of the present invention found that when a specimen from a subject suffering from atherosclerotic vascular disease is analyzed by gradient gel electrophoresis analysis, the gel will show specific protein bands. In contrast, the electrophoresis gel provided from a gradient gel electrophoresis analysis of a specimen from a subject who does not suffer from atherosclerotic vascular disease (i.e., a healthy subject or a subject suffering from other diseases) normally shows a significantly different protein band pattern. Therefore, the gradient gel electrophoresis analysis can be used to determine if a subject is at high risk for developing atherosclerotic vascular disease.

Accordingly, the present invention provides a method for rapidly and preliminary detecting whether a subject is at high risk for developing atherosclerotic vascular disease, comprising the following steps:

(1) providing a specimen from a subject;

(2) analyzing the specimen by using a gradient gel electrophoresis analysis; and (3) based on the results of the gel electrophoresis analysis in step (2), determining if the subject is at high risk for developing atherosclerotic vascular disease.

In step (1), the subject can be a human or a mammalian animal, though, preferably a human. The specimen can be, for example, blood or plasma, but is preferred to be high-density lipoprotein (HDL).

In the case of using high-density lipoprotein as the specimen of the present invention, the specimen may be prepared by the following steps. A specimen from a subject is processed by a density gradient ultracentrifugation to obtain a high-density lipoprotein layer with a density ranging from 1.063 g/mL to 1.21 g/mL. The high-density lipoprotein layer is then treated by protease inhibitors to prevent the oxidation and degradation of the high-density lipoprotein. Then, the high-density lipoprotein is dialyzed against a buffer solution (containing 20 mmol/L Tris-HCl, 0.5 mmol/L EDTA, and 0.02% $NaN_3$; pH 8.0) with 3 buffer changes in 36 hours to remove salts. Optionally, before performing the gel electrophoresis analysis, the high-density lipoprotein can be treated with a solvent (e.g., ethyl acetate:ethanol=1:1) to remove the lipid embedded in the high-density lipoprotein, thereby, purifying the high-density lipoprotein.

Any kind of gradient gel electrophoresis analysis which is suitable for separating protein can be used in step (2), such as Bis-Tris gradient gel electrophoresis analysis or Tris-Glycine gradient gel electrophoresis analysis. Preferably, the gradient gel electrophoresis analysis in step (2) is a 4% to 12% Tris-Glycine gradient gel electrophoresis analysis, and more preferably, a 4% to 12% Bis-Tris gradient gel electrophoresis analysis.

When the gel electrophoresis analysis shows the following results, the subject is determined as being at high risk for developing atherosclerotic vascular disease:

(a) a first protein band with a molecular weight of about 28,380 daltons to about 28,400 daltons; and (b) at least one of:

(b1) a second protein band adjacent to the first protein band, with a molecular weight lower than that of the first protein band, and a tint identical to or lighter than that of the first protein band; and (b2) a third protein band adjacent to the first protein band, with a molecular weight higher than that of the first protein band, wherein the second protein band preferably has a molecular weight of about 28,000 daltons to about 28,100 daltons, and more preferably has a molecular weight of about 28,079 daltons. The term "adjacent" used in this specification (and the claims) refers to that, in the electrophoresis picture of a gel electrophoresis analysis, two protein bands are adjoining to each other and the difference between the molecular weights of the two protein bands is less than 500 daltons.

It has been confirmed by the inventors of the present invention that the second protein band is apolipoprotein A1 (ApoA1), while the first protein band and third protein band are protein isomers of apolipoprotein A1. It is known that ApoA1 is a major structural protein in high-density lipoprotein, with a molecular weight of about 28 kilodaltons. Without being limited by theory, it is believed that the first protein band and the third protein band are protein isomers formed by the protein modification of ApoA1. The modifications could be such as oxidation, glycation, formylation modifications, and the likes.

Because the method of the present invention is carried out by using a common and easy-operating gradient gel electrophoresis which only needs a little sample to conduct the detection, it has low-costs, easy operation and rapid detection. Therefore, the method of the present invention can be used in routine health examinations to help in disease management.

The present invention will be further illustrated in details with specific examples as follows. However, the following examples are provided only for illustrating the present invention, and the scope of the present invention is not limited thereby.

EXAMPLE

Example 1

Preparation of the Specimens to be Analyzed (1) The Subjects to be Analyzed

Eighteen subjects were selected. Of the eighteen, 3 were healthy subjects who did not suffer from atherosclerosis (the normal group; separately numbered as N1 to N3) and 15 subjects (the experimental group). In the experimental group there were 4 diabetic patients, separately numbered as DM1 to DM4; 5 uremic patients, separately numbered as UM1 to UM5; and 6 primary hyperlipidemic patients, separately numbered as HP1 to HP6. Diabetes, uremia, and primary hyperlipidemia are all risk factors for atherosclerosis. In the experimental group, seven subjects (DM1, UM1, UM2, HP1, HP2, HP3, and HP4) were diagnosed with atherosclerotic vascular disease (includes coronary artery disease, ischemic stroke, and/or carotid artery disease).

Table 1 shows the age, gender, disease status, and the concentration of triglycerides, cholesterol, low-density lipoprotein and high-density lipoprotein of the seven patients with atherosclerotic vascular disease in the experimental group.

TABLE 1

| Subject | | DM1 | UM1 | UM2 | HP1 | HP2 | HP3 | HP4 |
|---|---|---|---|---|---|---|---|---|
| Age (years) | | 58 | 58 | 73 | 57 | 42 | 34 | 53 |
| Gender | | female | male | female | male | male | male | male |
| Atherosclerotic vascular disease | Coronary artery disease | Y | Y | Y | Y | N | N | N |
| | Ischemic stroke | Y | Y | Y | N | Y | N | Y |
| | Carotid artery disease | Y | Y | Y | N/A | Y | Y | Y |
| Triglycerides (mg/dl) | | 250 | 460 | 558 | 576 | 569 | 2997 | 102 |
| Cholesterol (mg/dl) | | 261 | 228 | 224 | 210 | 92 | 308 | 245 |
| Low-density lipoprotein (mg/dl) | | 178 | 112 | 136 | 157 | 39 | 48 | 161 |
| High-density lipoprotein (mg/dl) | | 33 | 34 | 35 | 34 | 31 | 22 | 38 |

Y: exist; N: non-exist; N/A: data not available.

(2) Preparation of Specimens

The fasting venous blood (20 mL) of the subjects described in the above item (1) were analyzed by sequential density gradient ultracentrifugation (Optima™ L-90k, Beckman Coulter, USA) to obtain a high-density lipoprotein layer with a density ranging from 1.063 g/mL to 1.21 g/mL. Then, a cocktail protease inhibitor (Roche), 1% PSN antibiotics (GIBCO), 0.02 w/v % $NaN_3$, 10 mmol/L $Na_4P_2O_7$, 1 mmol/L $Na_3VO_4$, and 10 mmol/L β-glycerophosphate were added immediately into the high-density lipoprotein layer to protect the high-density lipoprotein from oxidation and degradation.

Then, the high-density lipoprotein layer was dialyzed against a buffer solution (contains 20 mmol/L Tris-HCl, 0.5 mmol/L EDTA, and 0.02% NaN$_3$; pH 8.0) with 3 buffer changes in 36 hours to remove the salts.

Example 2

Gel Electrophoresis Analysis

The high-density lipoprotein obtained from Example 1 was delipidated with a solvent (e.g., ethyl acetate:ethanol=1:1), and then, was dissolved in 10% SDS and analyzed by the following gel electrophoresis analysis:
(1) Performing a 10% Tris-Glycine SDS-PAGE at room temperature with a voltage at 110 V; and
(2) Performing a 4% to 12% Bis-Tris gradient gel electrophoresis (NuPAGE®, Invitrogen, USA) at room temperature with a voltage at 135 V.
When the gel electrophoresis was finished, the electrophoresis gels were stained with Coomassie blue G-250. The results are shown in FIGS. 1A and 1B.

Figure 1B:
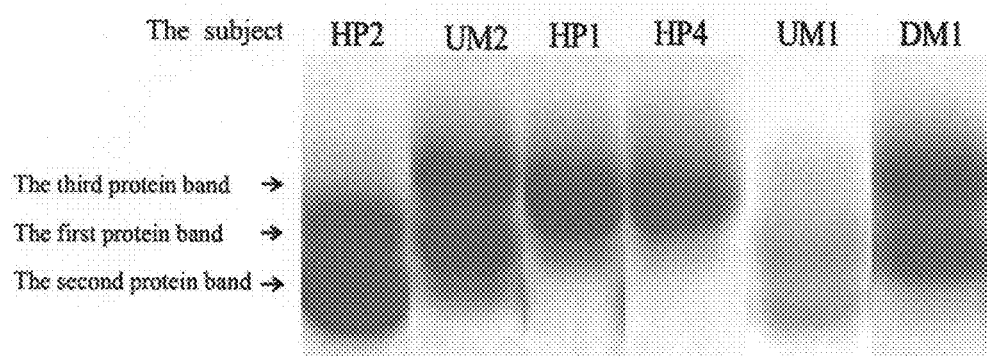

FIGS. 1A and 1B show the protein bands of apolipoprotein A1 (ApoA1; has a molecular weight of about 28 kilodaltons) separated from the high-density lipoprotein samples by the gel electrophoresis analysis. As shown in FIG. 1A (the above figure), when the high-density lipoprotein specimens were analyzed by 10% SDS-PAGE, all of the specimens only show a single protein band of ApoA1. These results indicate that 10% SDS-PAGE can not be used to determine if a subject is at high risk for developing atherosclerotic vascular disease. In contrast, as shown in FIG. 1A (the below figure), when the high-density lipoprotein samples were analyzed by 4% to 12% Bis-Tris gradient gel electrophoresis, the specimens from the healthy group and the subject who did not suffer from atherosclerotic vascular disease in the experimental group show two protein bands of ApoA1 protein isomers, i.e., the first protein band and the second protein band indicated by the arrows shown in FIGS. 1A and 1B, and the second protein band has a tint significantly darker than that of the first protein band.

In another aspect, as shown in FIGS. 1A (the below figure) and 1B, the specimens from the subjects numbered as HP3 or UM2 show three protein bands of ApoA1 protein isomers, i.e., the first protein band, the second protein band and the third protein band. The specimens from the subjects numbered as HP2 or UM1 show two protein bands of ApoA1 protein isomers, i.e., the first protein band and the second protein band, and the second protein band has a tint identical to or lighter than that of the first protein band. The specimens from the subjects numbered as HP1, HP4 or DM1 show two protein bands of ApoA1 protein isomers, i.e., the first protein band and the third protein band.

The above results show that when the high-density lipoprotein specimens from the patients suffering from atherosclerotic vascular disease (i.e., DM1, UM1, UM2, HP1, HP2, HP3, and HP4) were analyzed by the 4% to 12% Bis-Tris gradient gel electrophoresis, the electrophoresis gel show (a) a first protein band; and (b) at least one of:
(b1) a second protein band adjacent to the first protein band, with a molecular weight lower than that of the first protein band, and a tint identical to or lighter than that of the first protein band; and
(b2) a third protein band adjacent to the first protein band, with a molecular weight higher than that of the first protein band.

Example 3

Matrix-Assisted Laser Desorption Ionization-Time of Flight (MALDI-TOF) Mass Spectrometry (1) Determination of Protein Molecular Weight The first protein band, the second protein band and the third protein band on the gels shown in the FIGS. 1A (the below figure) and 1B were excised and sliced into small pieces. The sliced gel pieces were de-stained with a buffer solution (50% acetonitrile and 0.1% trifluoroacetic acid), dried by a centrifugal concentrator (miVac Duo Concentrator, Genevac, USA), and then incubated in 0.1% formic acid with gentle agitation to extract the protein from the gel.

Figure 2:
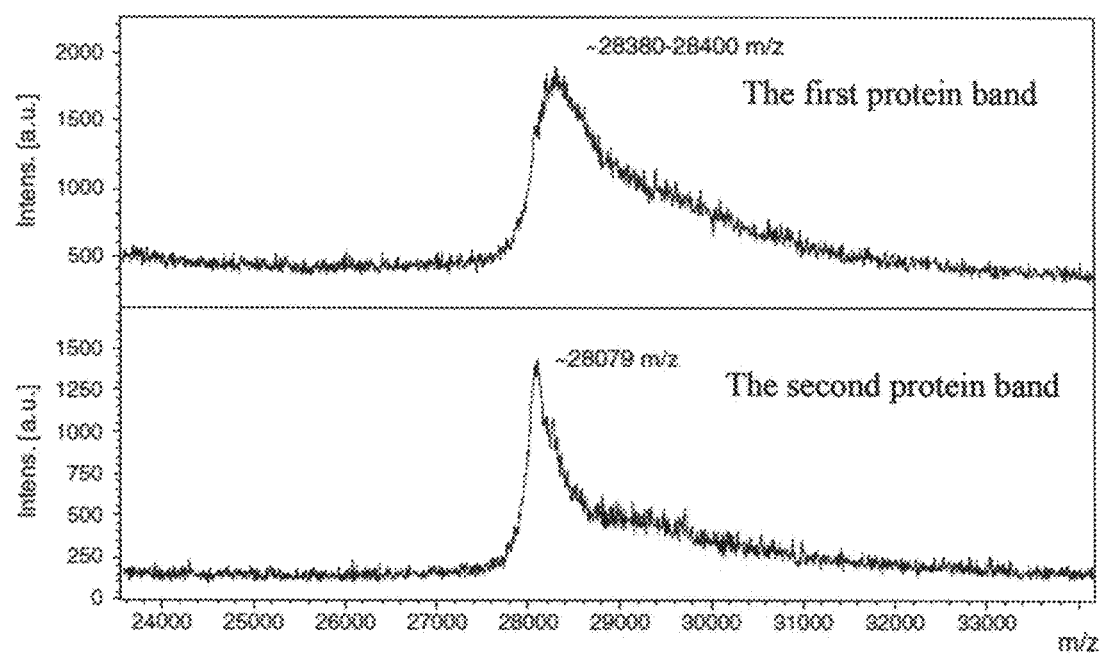
FIG. 2 is a MALDI-TOF mass spectrum of the first protein band and the second protein band shown on the electrophoresis gel of example 1.

Then, the extracted protein samples were analyzed by matrix-assisted laser desorption ionization-time of flight mass spectrometry (MALDI-TOF; Ultraflex III TOF/TOF, BrukerDaltonics), and a peptide calibration standard kit (BrukerDaltonics) was used to determine the molecular weight of the protein samples. The parameters of the mass spectrometry were set as follows: linear mode; 25 kV accelerating voltage; 100 ns pulsed ion extraction time. The results are shown in FIG. 2.

(2) Identification of Protein Types

The first protein band, the second protein band and the third protein band on the gels shown in the FIGS. 1A (the below figure) and 1B were excised and sliced into small pieces. The sliced gel pieces were subjected to in-gel digestion with the following steps: thrice washed with a 25 mmol/L ammonium bicarbonate solution (pH 8.2) containing 50% acetonitrile for 15 min; dehydrated with 100% acetonitrile, reduced by 10 mmol/L dithiothreitol (DTT) at 56° C. for 15 minutes; alkylated with 55 mmol/L indoleacetic acid (IAA) in the dark at room temperature for 20 minutes; and washed with a 25 mmol/ammonium bicarbonate solution (pH 8.2) containing 50% acetonitrile for 10 min. Then, the sliced gel pieces were treated with trypsin at 37° C. for 12 hours to digest the proteins therein, and incubated in 50% acetonitrile containing 0.1% trifluoroacetic acid to extracted the digested proteins from the gel.

The extracted solution containing peptides were dried by a centrifugal concentrator, re-dissolved, and then analyzed by MALDI-TOF mass spectrometry. The parameters of the mass spectrometry were set as follows: reflector mode; 25 kV accelerating voltage; 26.3 kV reflector voltage; and 20 ns pulsed ion extraction time. Then, the experimental data were inputted into the SwissProt protein database to conduct a peptide mass fingerprinting (PMF) analysis to identify the protein types.

(3) Result

The results of the MALDI-TOF mass spectrometry and the comparison results against SwissProt protein database demonstrate that after the specimens from the subject suffering from atherosclerotic vascular disease were analyzed by a 4% to 12% Bis-Tris gradient gel electrophoresis analysis, the first protein band, the second protein band, and the third protein band shown on the electrophoresis gel are human ApoA1 (GenBank ID: AAH05380.1).

As shown in FIG. 2, the molecular weight of the second protein band is about 28,079 daltons. The molecular weight of the first protein band ranges from about 28,380 daltons to about 28,400 daltons. The mass spectrum of the first protein band shows a significant high-mass peak tailing, revealing that the first protein band may be a protein formed by diverse modifications (rather than a single modification) of ApoA1. In addition, the molecular weight of the third protein band was not successfully obtained in this experiment, possibly due to more diverse modifications or a higher negatively-charged modification level of ApoA1, which results in a great decrease in detection sensitivity.

The above results show that the molecular weight of the ApoA1 in the high-density lipoprotein specimen from a patient suffering from atherosclerotic vascular disease is about 28,079 daltons, and that the ApoA1 can be modified to form its protein isomers with a greater molecular weight than that of ApoA1 (i.e., the first protein band and the third protein band shown on the gel of the gradient gel electrophoresis analysis). The first protein band has a molecular weight that ranges from about 28,380 daltons to about 28,400 daltons).

Therefore, when the gel electrophoresis analysis shows the following results, the subject is determined as being at high risk of developing atherosclerotic vascular disease:
(a) a first protein band with a molecular weight of about 28,380 daltons to about 28,400 daltons; and
(b) at least one of:
(b1) a second protein band adjacent to the first protein band with a molecular weight lower than that of the first protein band, and a tint identical to or lighter than that of the first protein band; and
(b2) a third protein band adjacent to the first protein band with a molecular weight higher than that of the first protein band.

Example 4

Clinical Screening

Seven voluntary subjects (separately numbered as "a" to "g") were selected from clinical diabetic patients to conduct the following screening. High-density lipoprotein specimens were purified from the fasting venous blood (20 mL) of each subject according to the method described in item (2) of example 1. The purified high-density lipoprotein specimens were analyzed by a 4% to 12% Bis-Tris gradient gel electrophoresis analysis. Then, the protein band profile shown on the electrophoresis gel of each subject determined if that subject was at high risk for developing atherosclerotic vascular disease. After the completed screening, the physical condition of each subject was followed to confirm if the subject who was determined as being at high risk for developing atherosclerotic vascular disease actually developed atherosclerotic vascular disease in a certain time period.

Figure 3:
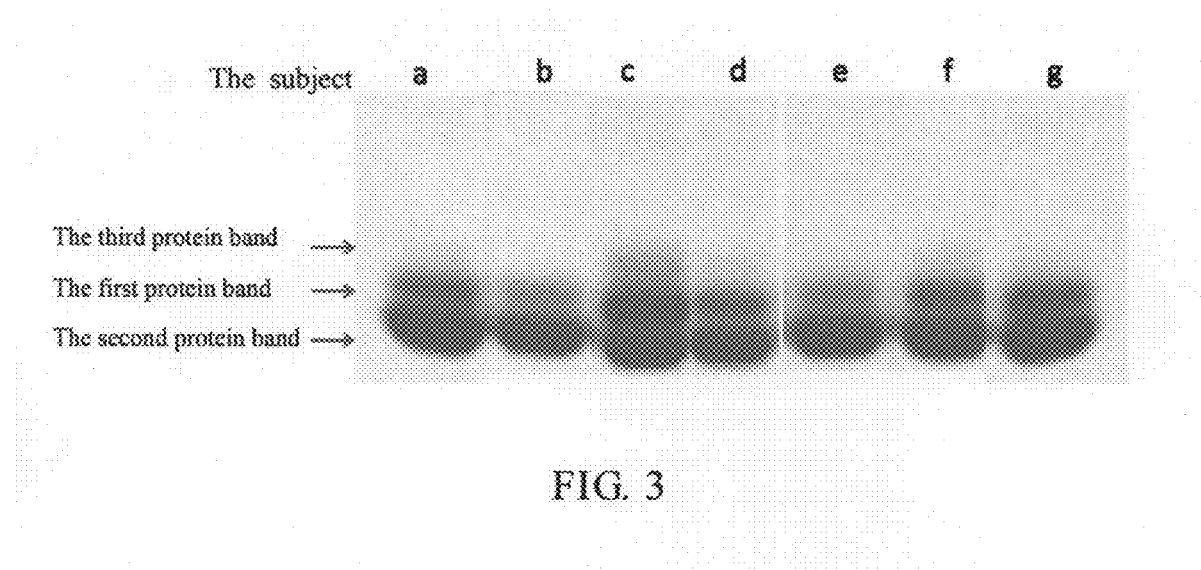
FIG. 3 is a 4% to 12% Bis-Tris gradient gel electrophoresis picture of the high-density lipoprotein obtained from the clinical subjects.

Among the above subjects, after the high-density lipoprotein of one subject (numbered as "c") was analyzed by a 4% to 12% Bis-Tris gradient gel electrophoresis analysis, the electrophoresis gel showed the first protein band, the second protein band, and the third protein band (as shown in FIG. 3). Accordingly, the subject was determined to be at high risk for developing atherosclerotic vascular disease. In the follow-up study, it was discovered that the subject was diagnosed with left common femoral arterial occlusive disease (i.e., a peripheral arterial occlusive disease) three months after the aforesaid screening. These results show that the method of the present invention indeed can be used to determine if a subject is at high risk for developing atherosclerotic vascular disease, thereby aiding in disease prevention and management.

The above examples are merely exemplified to illustrate the principle and efficacy of the present invention, but are not intended to limit the present invention. It is obvious to those skilled in the art that the various changes and modifications can be made in the technical spirit of the present invention, and thus, it is apparent that these changes and modifications are included within the scope of the appended claims and their equivalents.

What is claimed is:

1. A method for diagnosing whether a subject is at high risk for developing atherosclerotic vascular disease (ASVD), comprising:
(1) providing a specimen from a subject;
(2) analyzing the specimen by using a gradient gel electrophoresis analysis; and
(3) based on the results of the gel electrophoresis analysis in step (2), determining if the subject is at high risk for developing atherosclerotic vascular disease,
wherein the gradient gel electrophoresis analysis in step (2) is a 4% to 12% Bis-Tris gradient gel electrophoresis analysis,
and wherein in step (3), the subject is determined as being at high risk for developing atherosclerotic vascular disease if the gel electrophoresis analysis shows the following results:
(a) a first protein band with a molecular weight of about 28,380 daltons to about 28,400 daltons; and
(b) at least one of:
(b1) a second protein band adjacent to the first protein band, with a molecular weight lower than that of the first protein band and a tint identical to or lighter than that of the first protein band; and
(b2) a third protein band adjacent to the first protein band, with a molecular weight higher than that of the first protein band.

2. The method as claimed in claim 1, wherein the subject is a human.

3. The method as claimed in claim 1, wherein the specimen in step (1) is blood, plasma, or high-density lipoprotein.

4. The method as claimed in claim 1, wherein the second protein band has a molecular weight of about 28,000 daltons to about 28,100 daltons.

5. The method as claimed in claim 1, wherein the second protein band has a molecular weight of about 28,079 daltons.

6. A method for diagnosing whether a subject is at high risk for developing atherosclerotic vascular disease (ASVD), comprising:
(1) providing a specimen from a subject;
(2) analyzing the specimen by using a gradient gel electrophoresis analysis; and
(3) based on the results of the gel electrophoresis analysis in step (2), determining if the subject is at high risk for developing atherosclerotic vascular disease,
wherein the gradient gel electrophoresis analysis in step (2) is a 4% to 12% Bis-Tris gradient gel electrophoresis analysis or a 4% to 12% Tris-Glycine gradient gel electrophoresis analysis, and wherein in step (3), the subject is determined as being at high risk for developing atherosclerotic vascular disease if the gel electrophoresis analysis shows the following results:
(a) a first protein band with a molecular weight of about 28,380 daltons to about 28,400 daltons; and
(b) at least one of:
(b1) a second protein band adjacent to the first protein band, with a molecular weight lower than that of the first protein band and a tint identical to or lighter than that of the first protein band; and
(b2) a third protein band adjacent to the first protein band, with a molecular weight higher than that of the first protein band.

7. The method as claimed in claim 6, wherein the second protein band has a molecular weight of about 28,000 daltons to about 28,100 daltons.

8. The method as claimed in claim 6, wherein the second protein band has a molecular weight of about 28,079 daltons.

* * * * *